(12) United States Patent
Tomkinson (10) Patent No.: US 9,487,525 B2
(45) Date of Patent: Nov. 8, 2016

(54) CRYSTALLINE FORMS OF (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

(71) Applicant: ASTRAZENECA AB, Sodertalje (SE)

(72) Inventor: Gary Peter Tomkinson, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 14/394,918

(22) PCT Filed: Apr. 16, 2013

(86) PCT No.: PCT/GB2013/050973
§ 371 (c)(1),
(2) Date: Oct. 16, 2014

(87) PCT Pub. No.: WO2013/156772
PCT Pub. Date: Oct. 24, 2013

(65) Prior Publication Data
US 2015/0087661 A1    Mar. 26, 2015

Related U.S. Application Data

(60) Provisional application No. 61/625,312, filed on Apr. 17, 2012.

(51) Int. Cl.
*C07D 487/04* (2006.01)
(52) U.S. Cl.
CPC .................................. *C07D 487/04* (2013.01)
(58) Field of Classification Search
None
See application file for complete search history.

(56) References Cited

U.S. PATENT DOCUMENTS

| | | |
|---|---|---|
| 5,439,686 A | 8/1995 | Desai et al. |
| 6,162,804 A | 12/2000 | Bilodeau |
| 6,432,947 B1 | 8/2002 | Arnaiz et al. |
| 6,749,868 B1 | 6/2004 | Desai et al. |
| 2002/0094974 A1 | 7/2002 | Castelhano et al. |
| 2003/0045536 A1 | 3/2003 | Castelhano et al. |
| 2003/0073708 A1 | 4/2003 | Castelhano et al. |
| 2003/0139427 A1 | 7/2003 | Castelhano et al. |
| 2004/0014694 A1 | 1/2004 | Chakroun |
| 2004/0082598 A1 | 4/2004 | Castelhano et al. |
| 2004/0082599 A1 | 4/2004 | Castelhano et al. |

(Continued)

FOREIGN PATENT DOCUMENTS

| | | |
|---|---|---|
| EP | 0100172 B1 | 8/1987 |
| EP | 1444982 B1 | 8/2004 |

(Continued)

OTHER PUBLICATIONS

Abhijit M. Godbole et al, "New insights into the Androgen Targeted Therapies and Epidgenetic Therapies in prostate cancer", Prostate Cancer, vol. 2011, Oct. 12, 2011, pp. 1-13 XP055057925.

(Continued)

*Primary Examiner* — Anna Pagonakis
(74) *Attorney, Agent, or Firm* — Daniel Kopp (57) ABSTRACT

The present invention discloses certain new solid state forms of (S)-4-amino-N-(1-(4-chlorophenyl)-3-hydroxypropyl)-1-(7H-pyrrolo[2,3-d]pyrimidin-4-yl)piperidine-4-carboxamide, processes for preparing such forms, pharmaceutical compositions comprising them, and the use of such forms in therapy.

12 Claims, 8 Drawing Sheets

X-ray powder diffraction pattern – Form A of Compound (I)

(56) References Cited

U.S. PATENT DOCUMENTS

| | | | |
|---|---|---|---|
| 2006/0111362 A1 | 5/2006 | Kira et al. | |
| 2006/0148844 A1 | 7/2006 | Nakade et al. | |
| 2006/0287528 A1* | 12/2006 | Wenslow | C07D 87/04 544/350 |
| 2007/0082838 A1 | 4/2007 | De et al. | |
| 2007/0117744 A1 | 5/2007 | Desai et al. | |
| 2007/0135402 A1 | 6/2007 | Habashita et al. | |
| 2008/0070936 A1 | 3/2008 | Castelhano et al. | |
| 2008/0161382 A1 | 7/2008 | Desai et al. | |

FOREIGN PATENT DOCUMENTS

| | | |
|---|---|---|
| GB | 1047935 | 11/1966 |
| WO | 9320097 A1 | 10/1993 |
| WO | 9500516 A1 | 1/1995 |
| WO | 9738665 A2 | 10/1997 |
| WO | 9907703 A1 | 2/1999 |
| WO | 9962908 | 12/1999 |
| WO | 9965909 A1 | 12/1999 |
| WO | 0075145 A1 | 12/2000 |
| WO | 0107050 A1 | 2/2001 |
| WO | 01014371 A1 | 3/2001 |
| WO | 02000661 A1 | 1/2002 |
| WO | 02018348 A2 | 3/2002 |
| WO | 02057267 A1 | 7/2002 |
| WO | 02076484 A2 | 10/2002 |
| WO | 03057696 A1 | 7/2003 |
| WO | 03088908 A2 | 10/2003 |
| WO | 2004014850 A2 | 2/2004 |
| WO | 2004021979 A2 | 3/2004 |
| WO | 2004043380 A2 | 5/2004 |
| WO | 2004080463 A1 | 9/2004 |
| WO | 2004094426 A1 | 11/2004 |
| WO | 2005003128 A1 | 1/2005 |
| WO | 2005020921 A2 | 3/2005 |
| WO | 2005026149 A1 | 3/2005 |
| WO | 2005044181 A2 | 5/2005 |
| WO | 2005051304 A2 | 6/2005 |
| WO | 2005117909 A2 | 12/2005 |
| WO | 2006046023 A1 | 5/2006 |
| WO | 2006046024 A1 | 5/2006 |
| WO | 2006071819 A1 | 7/2006 |
| WO | 2006075094 A2 | 7/2006 |
| WO | 2006075095 A2 | 7/2006 |
| WO | 2006091450 A1 | 8/2006 |
| WO | 2006124118 A1 | 11/2006 |
| WO | 2006135639 A1 | 12/2006 |
| WO | 2007007919 A2 | 1/2007 |
| WO | 2007025090 A2 | 3/2007 |
| WO | 2007084667 A2 | 7/2007 |
| WO | 2007125310 A2 | 11/2007 |
| WO | 2007125315 A2 | 11/2007 |
| WO | 2007125320 A1 | 11/2007 |
| WO | 2007125321 A2 | 11/2007 |
| WO | 2007125325 A1 | 11/2007 |
| WO | 2008075109 A1 | 6/2008 |
| WO | 2008075110 A1 | 6/2008 |
| WO | 2008079346 A1 | 7/2008 |
| WO | 2009047563 A1 | 4/2009 |
| WO | WO 2009/047563 * | 4/2009 |
| WO | 2010092371 A1 | 8/2010 |
| WO | 2013079964 A1 | 6/2013 |

OTHER PUBLICATIONS

Bradley Mo et al. Tumor targeting by covalent conjugation of a natural fatty acid to paclitaxel; Clin. Cancer Res. 2001; 7: 3229-38.

Barnett et al, "The Akt-PKB Family of Protein Kinases: A Review of Small Molecule Inhibitors and Progress Towards Target Validation", Current Topics in Medicinal Chemistry, 2005, pp. 109-125, vol. 5.

quintela et al, "Pyrazolopyrimidines: synthesis, effect on histamine release from rat peritoneal mast cells and cytotoxic activity", Eur J Med Chem, 2001, pp. 321-332, vol. 36.

Apr. 22, 2010 IPRP for corresponding PCT application. Application No. PCT/GB2008/050925.

Aug. 20, 2010 Opposition filed against corresponding application in Dominican Republic, Patent Application No. P2010-0103.

Oct. 13, 2010 Opposition filed against corresponding application in Ecuador, Patent Application No. SP-10-10093.

Nov. 1, 2010 Opposition filed against corresponding application in Costa Rica, Patent Application No. 11.359.

Bales et al, Use of F-FDG PET as a biomarker to demonstrate activity of the novel AKT inhibitor AZD5363 in a Kenograft model, AACR Apr. 4, 2011, p. 1030.

Davies et al, Characterization of AZD5363, an orally bioavailable, potent ATP-competitive inhibitor of AKT kinases with pharmacodynamic and antitumor activity in preclinical models, AACR Apr. 4, 2011, p. 4477.

Greenwood et al, In vitro mechanism of action of AZD5363, a novel AKT inhibitor, in breast and prostate cancer cell lines, AACR Apr. 4, 2011, p. 1052.

Lamoureux et al, AZD5363 a novel Akt inhibitor delays prostate cancer progression by inhibiting androgen-receptor activity, The Vancouver Prostate Centre and AstraZeneca, Apr. 4, 2011.

Luke et al, Discovery of AZD5363 in orally bioavailable potent ATP-competitive inhibitor of AKT kinases, AACR Apr. 1, 2011, p. 4478.

MacKay, Transforming Drug Discovery Innovative Platforms, Pfizer, Nov. 30, 2006.

C. Harbron (Stat. Med. Jul. 20, 2010; 29(16): 1746-56).

Balbach et al., "Pharmaceutical evaluation of early development candidates "The 100 mg approach"" International Journal of Pharmaceutics, 2004, vol. 275, pp. 1-12.

Caira, "Crystalline polymorphism of organic compounds," Design of Organic Solids, Weber E et al., "ED", Springer, 1998.

Hlilfiker et al., Relevance of solid-state properties for pharmaceutical products—Chapter 1, Polymorphism: in the pharmaceutical industry. Edited by Rolf Hiner, Wiley 2006.

Singhal et al., "Drug polymorphism and dosage form design: a practical perspective," Advanced Drug Delivery Reviews, 2004, vol. 56, pp. 335-347.

Brittain et al., "ED": Polymorphism in pharmaceutical solids, Marcel Dekker Inc, New York, 1999.

* cited by examiner

Figure 1: X-ray powder diffraction pattern – Form A of Compound (I)

Figure 2: DSC thermogram – Form A of Compound (I)

Figure 3.1: X-ray powder diffraction pattern 1 – Form B of Compound (I)

Figure 3.2: X-ray powder diffraction pattern 2 – Form B of Compound (I)

Figure 4: DSC Thermogram 1 – Form B of Compound (I)

Figure 5: X-ray powder diffraction pattern – Form C of Compound (I)

Figure 6: DSC thermogram – Form C of Compound (I)

Figure 7: DSC Thermogram 2 – Form B of Compound (I)

CRYSTALLINE FORMS OF (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

CROSS-REFERENCE TO RELATED APPLICATIONS

This application is a 35 U.S.C. §371 national stage filing of International Application No. PCT/GB2013/050973, filed Apr. 16, 2013, and claims priority under 35 U.S.C. §119(e) to U.S. provisional application Ser. No. 61/625,312, filed Apr. 17, 2012, entitled "Crystalline Forms", the contents of which are hereby incorporated by reference.

FIELD OF THE INVENTION

The present invention discloses certain new solid state forms of (S)-4-amino-N-(1-(4-chlorophenyl)-3-hydroxypropyl)-1-(7H-pyrrolo[2,3-d]pyrimidin-4-yl)piperidine-4-carboxamide, processes for preparing such forms, pharmaceutical compositions comprising them, and the use of such forms in therapy.

BACKGROUND OF THE INVENTION

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active compound.

The different physical properties of the crystalline forms with respect to each other and with respect to the non-crystalline state may influence markedly the chemical and pharmaceutical processing of a compound, particularly when the compound is prepared or used on an industrial scale.

Further, in the manufacture of oral drug compositions, it is important that a reliable and reproducible plasma concentration profile of drug is provided following administration to a patient. Inter-patient variability in the absorption profile of a drug within the stomach, intestine or bloodstream can have an effect on drug safety and efficacy.

Chemical stability, solid state stability and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous materials may present problems in this regard. For example, such materials are typically difficult to handle and to formulate, provide for unreliable solubility, and are often found to be unstable and chemically impure.

The skilled person will appreciate that, if a drug can be readily obtained in a crystalline form that is also stable, one of more of the above problems may be solved.

Thus, in the manufacture of commercially viable, and pharmaceutically acceptable, drug compositions, it is important, wherever possible, to provide drug in a crystalline, and stable, form.

It is to be noted, however, that this goal is not always achievable. Indeed, typically, it is not possible to predict, from molecular structure alone, what the crystallisation behaviour of a compound (either alone or in the form of a salt) will be. This can only be determined empirically.

WO2009/047563, teaches a novel group of bicyclic heterocycles which may be useful in the treatment or prevention of a disease or medical condition mediated through protein kinase B (PKB, also known as AKT).

WO2009/047563 further discloses a specific bicyclic heterocycle identified therein as (S)-4-amino-N-(1-(4-chlorophenyl)-3-hydroxypropyl)-1-(7H-pyrrolo[2,3-d]pyrimidin-4-yl)piperidine-4-carboxamide (Example 9). This compound is designated herein as "Compound (I)", and is alternatively known as "AZD5363".

Compound (I)

Compound (I) has been shown to exhibit potent activity against all 3 mammalian isoforms of the AKT enzyme—with an $IC_{50}$ of 3 nM against AKT1, an $IC_{50}$ of 7 nM against AKT2 and an $IC_{50}$ of 7 nM against AKT3. Compound (I) is currently being developed as a potential new drug for the treatment of several different forms of cancer, either as a monotherapy or as part of a combination therapy.

WO2009/047563 further discloses three processes for the preparation of Compound (I)—Example 9 itself and alternative routes 1 and 2 for Example 9. "Example 9 alternative route 1" includes a slimy of Compound (I) in ethyl acetate and the other two processes isolate Compound (I) as a solid by evaporating fractions eluted from as column. The present inventor analysed (by XRD) three historical hatches of Compound (I) from our compound collection which were synthesised using a procedure identical to, or substantially similar to, one of these three processes and identified all three as being a semi-crystalline form, designated as "Form A".

DISCLOSURE OF THE INVENTION

We have now found that Compound (I) can be obtained in as number of different solid forms. Two of these new solid forms are referred to hereafter as "Form B" and "Form C". Form B is crystalline and Form C is semi-crystalline in nature. Analysis by XRD has determined that these forms are new forms and that Form A did not contain any Form B or C material.

Thus in the first aspect of the invention, there is provided Compound (I) in crystalline form.

In an alternative aspect of the invention, Compound (I) in crystalline form is in the form of Form B.

By "crystalline" we include greater than 80% crystalline, particularly greater than 90%, and more particularly greater than 95%. Most preferably "crystalline" is greater than 98%. By "semi-crystalline" we include greater than 5% but less than 80% crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

The crystalline form of the invention can have improved properties, for example stability, for example when compared with Compound (I) prepared as described in WO2009/047563.

According to a further aspect of the invention, there is thus provided a stable crystalline form of Compound (I). In particular this stable crystalline form of Compound (I) is Form B. The present inventor has found that a slurry of Form A in a suitable organic solvent, for example acetonitrile stirred for an appropriate length of time, for example 3 days, yields Form B. Form B can also be obtained by stirring a slurry of Form C in a suitable organic solvent such as acetone or isopropyl alcohol (IPA) for an appropriate amount of time. In view of these conversions over time of other Forms to Form B, the present inventor has concluded that Form B is most likely to be the thermodynamically most stable form. It is therefore predicted that Form B has beneficial properties when compared to other forms of Compound (I) for example in terms of its stability and therefore its propensity to convert or partially convert into other less desirable solid forms. This makes Form B potentially advantageous for assuring a longer product shelf-life and minimising any inter-patient variability and intra-patient variability of Compound (I) absorption.

The term "stability" as defined herein includes chemical stability and/or solid state stability.

By "chemical stability", we include that the respective compounds can be stored in an isolated form, or in the form of a formulation in which it is provided in admixture with pharmaceutically acceptable carriers, diluents or adjuvants (e.g. in an oral dosage form, such as tablet, capsule etc.), under normal storage conditions, with a limited degree of chemical degradation or decomposition.

By "solid state stability", we include that the respective compounds can be stored in an isolated solid form, or in the form of a solid formulation in which it is provided in admixture with pharmaceutically acceptable carriers, diluents or adjuvants (e.g. in an oral dosage form, such as tablet, capsule etc.), under normal storage conditions, with an insignificant degree of solid state transformation (e.g. crystallisation, recrystallisation, solid state phase transition, hydration, dehydration, solvation or desolvation).

Examples of "normal storage conditions" include temperatures of between minus 80° C. and plus 50° C. (particularly between 0° C. and 40° C. and more particularly room temperatures, such as 15° C. to 30° C.), pressures of between 0.1 and 2 bars (particularly at atmospheric pressure), relative humidities of between 5 and 95% (particularly 10 to 75%), and/or exposure to 460 lux of UV/visible light, for prolonged periods (i.e. greater than or equal to six months). Under such conditions, the crystalline forms of the invention may be found to be less than 15%, more particularly less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

According to a further aspect of the invention, there is provided a process for the production of Compound (I) in crystalline form in the form of Form B, which comprises stirring a slurry of Compound (I), particularly Compound (I) in the form of Form A or Form C, more particularly Form A, in a suitable solvent such as acetone or acetonitrile, particularly acetonitrile, followed by filtering and drying. In such a process it is important to leave the slurry to stir for a sufficient period of time in order to achieve optimum conversion to Form B. The length of time may also depend on the temperature of the slum. If the slurry is at 50° C. acceptable conversion yields may be achieved if the reaction is stirred for at least 3 days.

According to a further aspect, there is provided a process for the production of Compound (I) in the form of Form C, which comprises stirring a slurry of Compound (I), particularly Compound (I) in the form of Form A, in methanol followed by filtering and drying. In such a process it is important to leave the slurry to stir for a sufficient period of time in order to achieve full conversion to Form C. The length of time may also depend on the temperature of the slurry. If the slurry is at room temperature acceptable conversion yields may be achieved if the reaction is stirred for at least 3 days.

In an alternative aspect of the invent on Compound (I) in crystalline form is in the form of Form B and is substantially free of other Forms.

In an alternative aspect of the invention, Compound (I) in crystalline form is in the form of Form B and is substantially free of Form A.

In an alternative aspect of the invention, Compound (I) in crystalline form is in the form of Form B and is substantially free of Form C.

In an alternative aspect of the invention, Compound (I) in crystalline form is in the form of Form B and is substantially free of Form A and Form C.

In an alternative aspect, Compound (I) is in the form of Form C and is substantially free of other Forms.

In an alternative aspect, Compound (I) is in the form of Form C and is substantially free of Form A.

In an alternative aspect, Compound (I) is in the form of Form C and is substantially free of Form B.

In an alternative aspect, Compound (I) is in the form of Form C and is substantially free of Form A and Form B.

The term "substantially free" refers to less than 10% of another Form or Forms, preferably less than 5%.

Further information on the processes of the invention and the products obtainable there from are described in the Examples herein.

Crystalline forms of the invention may be isolated using techniques which are well known to those skilled in the an for example decanting, filtering or centrifuging. Crystalline forms of the invention may be dried using standard techniques. It will be appreciated by the skilled person that drying temperature and drying time may affect the solid state properties of compounds that are in the form of solvates (e.g. desolvation may occur at certain temperatures and/or reduced pressure).

The crystalline forms of the invention may be readily characterised using X-ray powder diffraction (XRPD) methods, for example as described hereinafter. Standard DSC and TGA techniques may also be used. ("TGA"=Thermogravimetric analysis).

Forms A, B and C of Compound (I) can be distinguished by reference to their onset of melting, powder X-ray diffraction patterns and/or single crystal X-ray data. In all of the claims, aspects and embodiments recited herein the peaks of the X-ray diffraction patterns are measured using CuKα radiation (i.e. X-rays with 1.54 Å wavelength).

Figure 1:
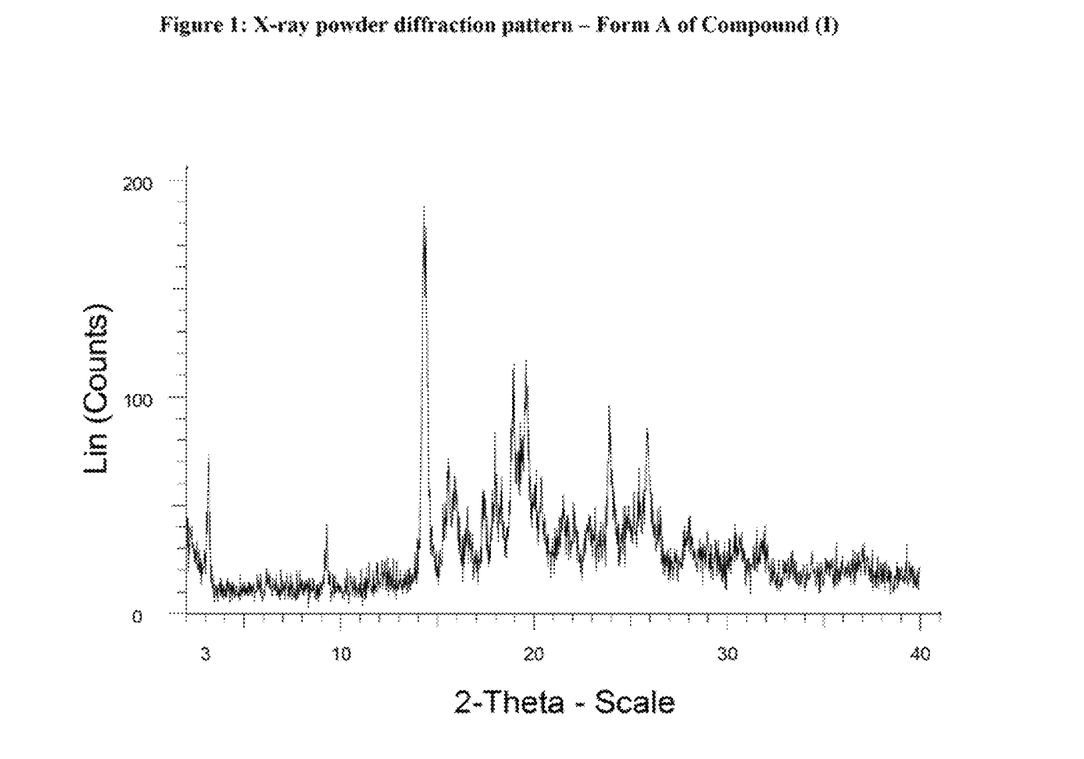
FIG. 1: X-ray powder diffraction pattern—Form A of Compound (I).

Form A of Compound (I) is characterised in providing an X-ray powder diffraction pattern substantially as shown in FIG. 1. Ten X-Ray powder diffraction peaks (obtained using 1.54 Å X-rays, i.e. CuKα radiation) are shown in Table A:

TABLE A

Ten X-Ray Powder Diffraction peaks for Form A of Compound (I)

| Angle (2θ): | 14.3 | 3.1 | 19.6 | 18.9 | 23.9 | 25.9 | 15.5 | 16.5 | 17.4 | 9.2 |
|---|---|---|---|---|---|---|---|---|---|---|
| Intensity (%): | 100 | 39.7 | 67.2 | 64.9 | 55.2 | 49.4 | 40.8 | 28.2 | 32.2 | 17.8 |

Accordingly Form A of Compound (I) has an X-ray powder diffraction pattern substantially the same as the X-ray powder diffraction pattern shown in FIG. 1.

Form A of Compound (I) provides X-ray powder diffraction patterns substantially the same as the X-ray powder diffraction patterns shown in FIG. 1 and has ten peaks [angle 2-theta (2θ) values] shown in Table A. It will be understood that the 2-theta values of the X-ray powder diffraction pattern may vary slightly front one machine to another or from one sample to another, and so the values quoted are not to be construed as absolute.

Figure 2:
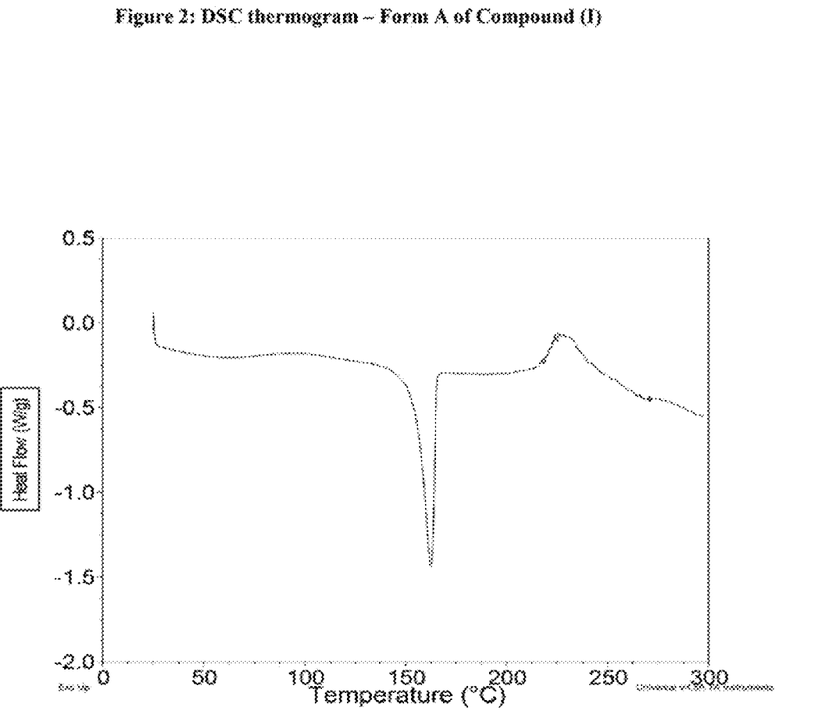
FIG. 2: DSC thermogram—Form A of Compound (I).

DSC analysis of Form A of Compound (I) shows a melting endotherm with an onset of 155.2° C. (FIG. 2).

Form B of Compound (I)

Figure 31:
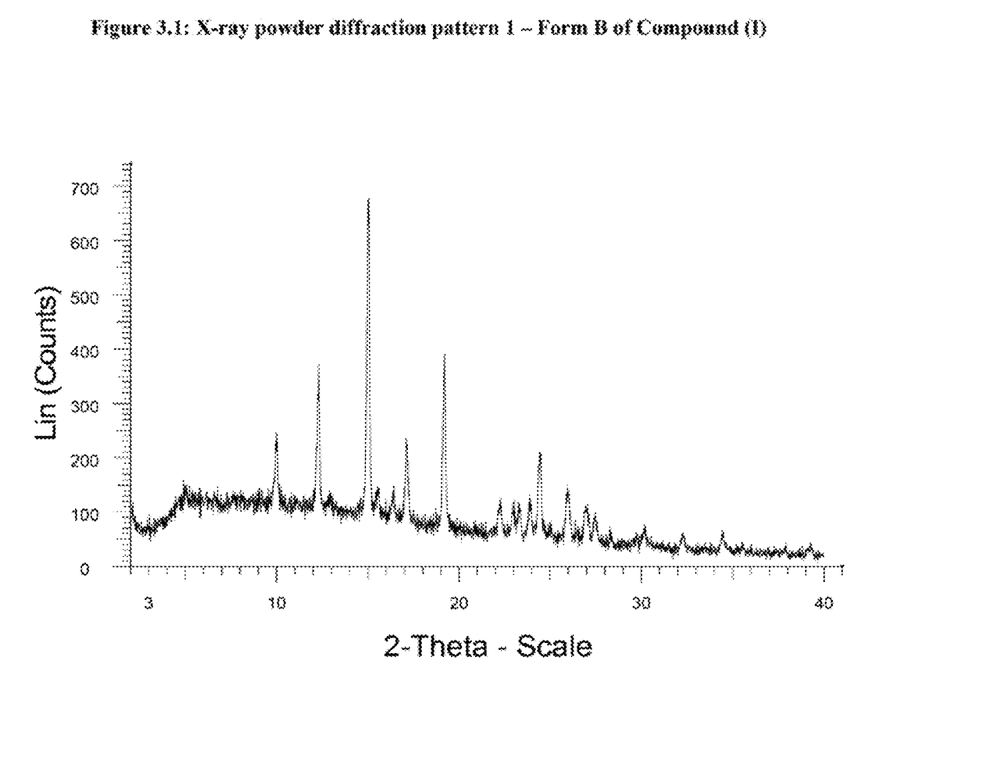

When Form B of Compound (I) was prepared by the method described hereinafter in 'Example 1' and analysed using a Bruker D8 X-ray powder diffractometer, the X-ray powder diffraction pattern of FIG. 3.1 was obtained (using 1.54 Å X-rays, i.e. CuKα radiation).

Accordingly, Form B of Compound (I) may be characterised in providing at least one of the following 2θ values measured using CuKα radiation 15.0 and 19.2. Form B may be characterised in providing an X-ray powder diffraction pattern substantially as shown in FIG. 3.1. Based on the X-ray diffraction pattern as shown in FIG. 3.1, ten X-Ray powder diffraction peaks (using 1.54 Å X-rays, i.e. CuKα radiation) relating to Form B are shown in Table B-1:

TABLE B-1

Ten X-Ray Diffraction peaks for Form B (based on FIG. 3.1)

| Angle (2θ): | 15.0 | 19.2 | 12.3 | 10.0 | 17.1 | 24.4 | 16.4 | 26.0 | 15.5 | 23.9 |
|---|---|---|---|---|---|---|---|---|---|---|
| Intensity (%): | 100 | 57.7 | 54.7 | 36.0 | 32.7 | 31.0 | 22.1 | 21.8 | 21.2 | 19.0 |

Figure 32:
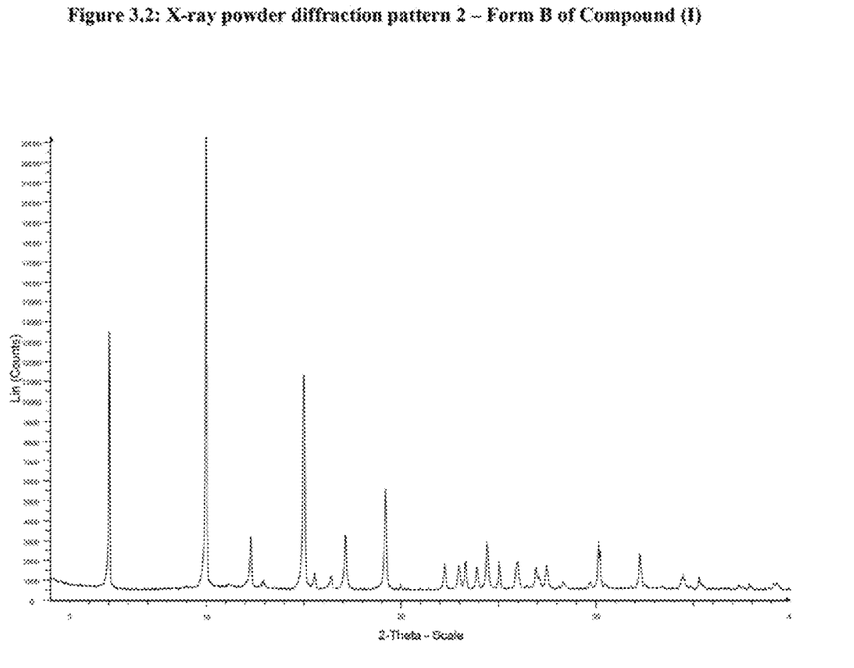

When Form B of Compound (I) was prepared by the method described hereinafter in 'Example 3' and analysed using a PANalytical CUBIX PRO X-ray powder diffractometer, where an improved signal-to-noise ratio was also achieved, the X-ray diffraction pattern of FIG. 3.2 was obtained (using 1.54 Å X-rays, i.e. CuKα radiation).

Accordingly, Form B may be characterised in providing an X-ray powder diffraction pattern substantially as shown in FIG. 3.2. Based on the X-ray diffraction pattern as shown in FIG. 3.2, ten X-ray powder diffraction peaks (using 1.54 Å X-rays, i.e. CuKα radiation) relating to Form B are shown in Table B-2:

TABLE B-2

| Ten X-Ray Diffraction peaks for Form B (based on FIG. 3.2) | | | | | | | | | | |
|---|---|---|---|---|---|---|---|---|---|---|
| Angle (2θ): | 10.0 | 5.0 | 15.0 | 19.2 | 17.1 | 12.3 | 24.4 | 30.2 | 32.3 | 23.3 |
| Intensity (%): | 100 | 57.8 | 48.7 | 24 | 14.1 | 13.8 | 12.4 | 11.4 | 9.8 | 8.2 |

According to the present invention there is provided a crystalline form, Form B of Compound (I), which has an X-ray powder diffraction pattern with at least one specific peak at about 2-theta=15.0°.

According to the present invention there is provided a crystalline form, Form B Compound (I), which has an X-ray powder diffraction pattern with at least one specific peak at about 2-theta=19.2°.

According to the present invention there is provided a crystalline form, Form B of Compound (I), which has an X-ray powder diffraction pattern with at least one specific peak at about 2-theta=12.3°.

According to the present invention there is provided a crystalline form, Form B of Compound (I), which has an X-ray powder diffraction pattern with at least two specific peaks at about 2-theta=15.0° and 19.2°.

According to the present invention there is provided a crystalline form, Form B of Compound (I), which has an X-ray powder diffraction pattern with at least three specific peaks at about 2-theta=12.3°, 15.0° and 19.2°.

According to the present invention there is provided a crystalline form, Form B of Compound (I), which has an X-ray powder diffraction pattern with specific peaks at about 2-theta=10.0, 12.3, 15.0, 17.1, 19.2 and 24.4°.

According to the present invention there is provided a crystalline form, Form B of Compound (I), which has an X-ray powder diffraction pattern with specific peaks at about 2-theta=15.0, 19.2, 12.3, 10.0, 17.1, 24.4, 16.4, 26.0, 15.5 and 23.9°.

According to the present invention there is provided a crystalline form, Form B of Compound (I), which has an X-ray powder diffraction pattern with specific peaks at about 2-theta=10.0, 5.0, 15.0, 19.2, 17.1, 12.3, 24.4, 30.2, 32.2 and 23.3°.

According to the present invention there is provided a crystalline form, Form B of Compound (I), which has an X-ray powder diffraction pattern substantially the same as the X-ray powder diffraction pattern shown in FIG. 3.1.

According to the present invention there is provided a crystalline form, Form B of Compound (I), which has an X-ray powder diffraction pattern substantially the same as the X-ray powder diffraction pattern shown in FIG. 3.2.

According to the present invention there is provided a crystalline form, Form B of Compound (I), which has an X-ray powder diffraction pattern with at least one specific peak at 2-theta=15.0° plus or minus 0.2° 2-theta.

According to the present invention there is provided a crystalline form, Form B of Compound (I), which has an X-ray powder diffraction pattern with at least one specific peak at 2-theta=19.2° plus or minus 0.2° 2-theta.

According to the present invention there is provided a crystalline form, Form B of Compound (I), which has an X-ray powder diffraction pattern with at least one specific peak at 2-theta=12.3° plus or minus 0.2° 2-theta.

According to the present invention there is provided a crystalline form, Form B of Compound (I), which has an X-ray powder diffraction pattern with at least two specific peaks at 2-theta=15.0° and 19.2° wherein said values may be plus or minus 0.2° 2-theta.

According to the present invention there is provided a crystalline form, Form B of Compound (I), which has an X-ray powder diffraction pattern with at least three specific peaks at 2-theta=12.3°, 15.0° and 19.2° wherein said values may be plus or minus 0.2° 2-theta.

According to the present invention there is provided a crystalline form, Form B of Compound (I), which has an X-ray powder diffraction pattern with specific peaks at 2-theta=10.0, 12.3, 15.0, 17.1, 19.2 and 24.4° wherein said values may be plus or minus 0.2° 2-theta.

According to the present invention there is provided a crystalline form, Form B of Compound (I), which has an X-ray powder diffraction pattern with specific peaks at 2-theta=15.0, 19.2, 12.3, 10.0, 17.1, 24.4, 16.4, 26.0, 15.5 and 23.9° wherein said values may be plus or minus 0.2° 2-theta.

According to the present invention there is provided a crystalline form, Form B of Compound (I), which has an X-ray powder diffraction pattern with specific peaks at 2-theta=10.0, 5.0, 15.0, 19.2, 17.1, 12.3, 24.4, 30.2, 32.2 and 23.3° wherein said values may be plus or minus 0.2° 2-theta.

According to the present invention there is provided a crystalline form, Form B of Compound (I), which has an X-ray powder diffraction pattern with at least one specific peak at 2-theta=15.0°.

According to the present invention there is provided a crystalline form, Form B of Compound (I), which has an X-ray powder diffraction pattern with at least one specific peak at 2-theta=19.2°.

According to the present invention there is provided a crystalline form, Form B of Compound (I), which has an X-ray powder diffraction pattern with at least one specific peak at 2-theta=12.3°.

According to the present invention there is provided a crystalline form, Form B of Compound (I), which has an X-ray powder diffraction pattern with at least two specific peaks at 2-theta=15.0° and 19.2°.

According to the present invention there is provided a crystalline form, Form B of Compound (I), which has an X-ray powder diffraction pattern with at least three specific peaks at 2-theta=12.3°, 15.0° and 19.2°.

According to the present invention there is provided a crystalline form, Form B of Compound (I), which has an X-ray powder diffraction pattern with specific peaks at 2-theta=10.0, 12.3, 15.0, 17.1, 19.2 and 24.4°.

According to the present invention there is provided a crystalline form, Form B of Compound (I), which has an X-ray powder diffraction pattern with specific peaks at 2-theta=15.0, 19.2, 12.3, 10.0, 17.1, 24.4, 16.4, 26.0, 15.5 and 23.9°.

According to the present invention there is provided a crystalline form, Form B of Compound (I), which has an X-ray powder diffraction pattern with specific peaks at 2-theta=10.0, 5.0, 15.0, 19.2, 17.1, 12.3, 24.4, 30.2, 32.2 and 23.3°.

According to the present invention there is provided a crystalline form, Form B of Compound (I), which has an X-ray powder diffraction pattern as shown in FIG. 3.1.

According to the present invention there is provided a crystalline form, Form B of Compound (I), which has an X-ray powder diffraction pattern as shown in FIG. 3.2.

Figure 4:
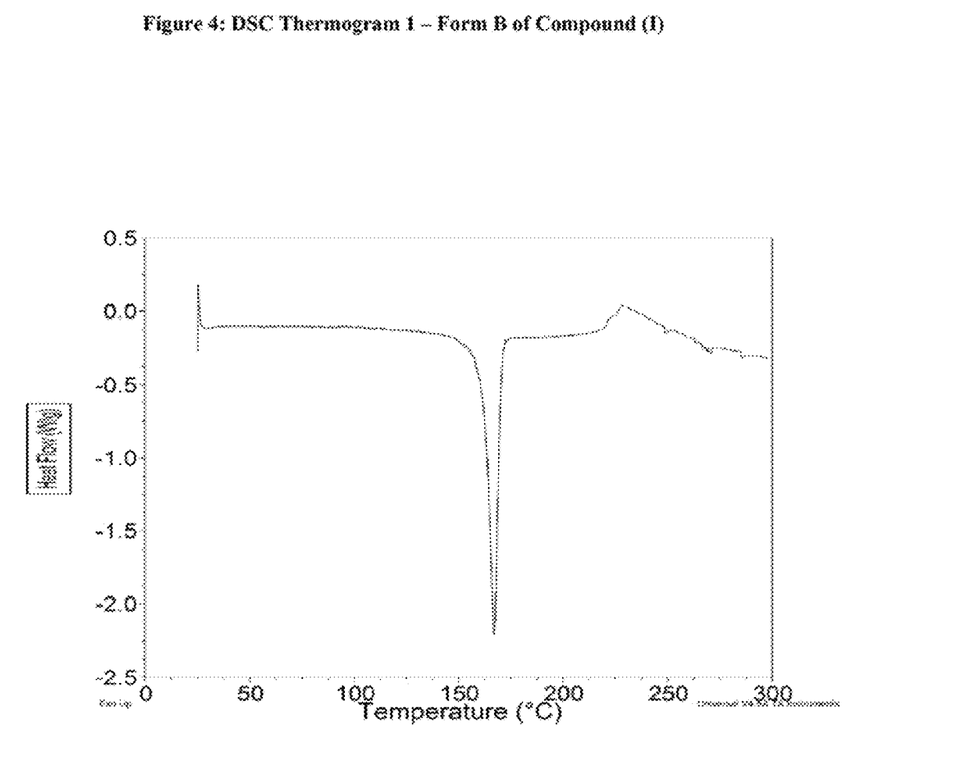
FIG. 4: DSC thermogram 1—Form B of Compound (I).

DSC analysis of Form B of Compound (I) [prepared by the method of Example 1, below] shows a melting endotherm with an onset of 162.3° C. and a peak at 167.1° C. (FIG. 4).

Figure 7:
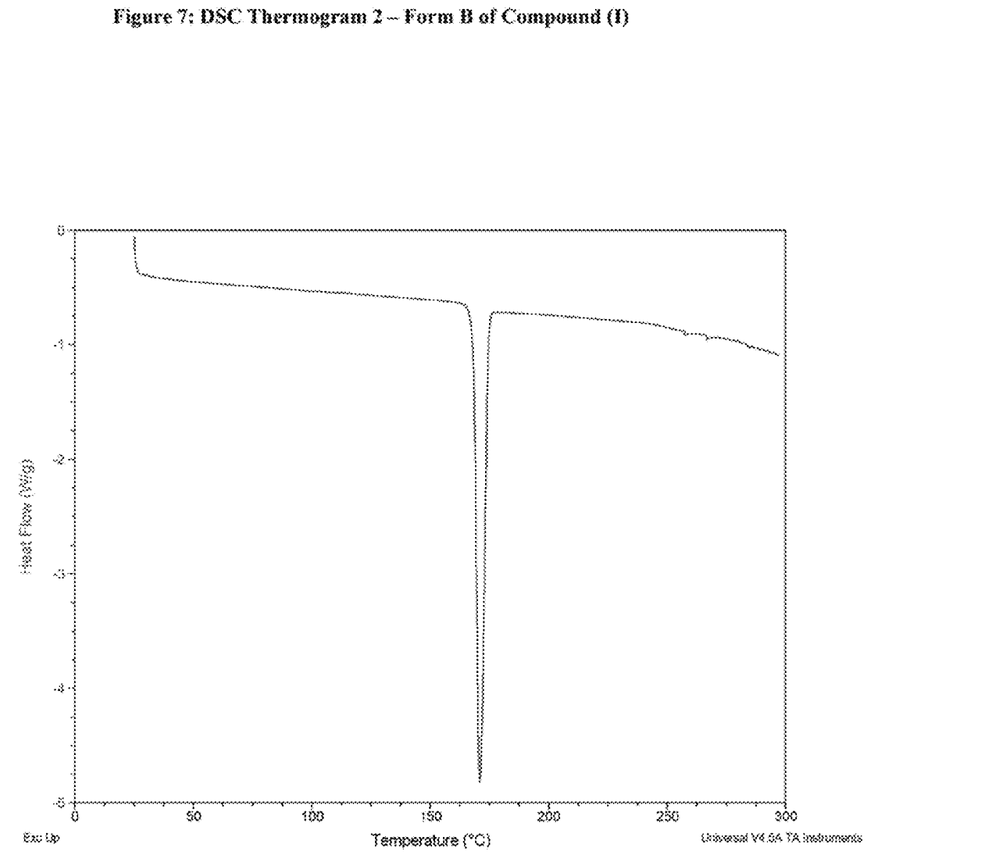
FIG. 7: DSC thermogram 2—Form B of Compound (I).

DSC analysis of Form B of Compound (I) [prepared by the method of Example 3, below] shows a melting endotherm with an onset of 168.5° C. and a peak at 171.0° C. (FIG. 7).

Accordingly, the Form B prepared by the method of Example 1 has a slightly lower melting point from the Form B as prepared by Example 3. It is speculated that this small difference in melting point arises because the Form B as prepared by the method of Example 3 is even more highly crystalline than the Form B as produced by the method of Example 1.

Thus DSC analysis shows Form B of Compound (I) may be a high melting solid with an onset of melting at about 162.3° C. and a peak at about 167.1° C.

Equally, DSC analysis shows Form B of Compound (I) may be a high melting solid with art onset of 168.5° C. and a peak at 171.0° C.

Accordingly, in any embodiment, aspect or claim herein, the Form B of Compound (I) has a melting point peak (as measured by DSC) within the range from 165° C. to 173° C.

Form B of Compound (I) provides X-ray powder diffraction patterns substantially the same as the X-ray powder diffraction patterns shown in FIGS. 3.1 and 3.2 and has the ten (angle 2-theta values) shown in Tables B-1 and B-2. It will be understood that the 2-theta values of the X-ray powder diffraction pattern may vary slightly from one machine to another or from one sample to another, and so the values quoted are not to be construed as absolute. Indeed, such variation is evident in FIGS. 3.1 and 3.2, and the corresponding Tables B-1 and B-2.

Figure 5:
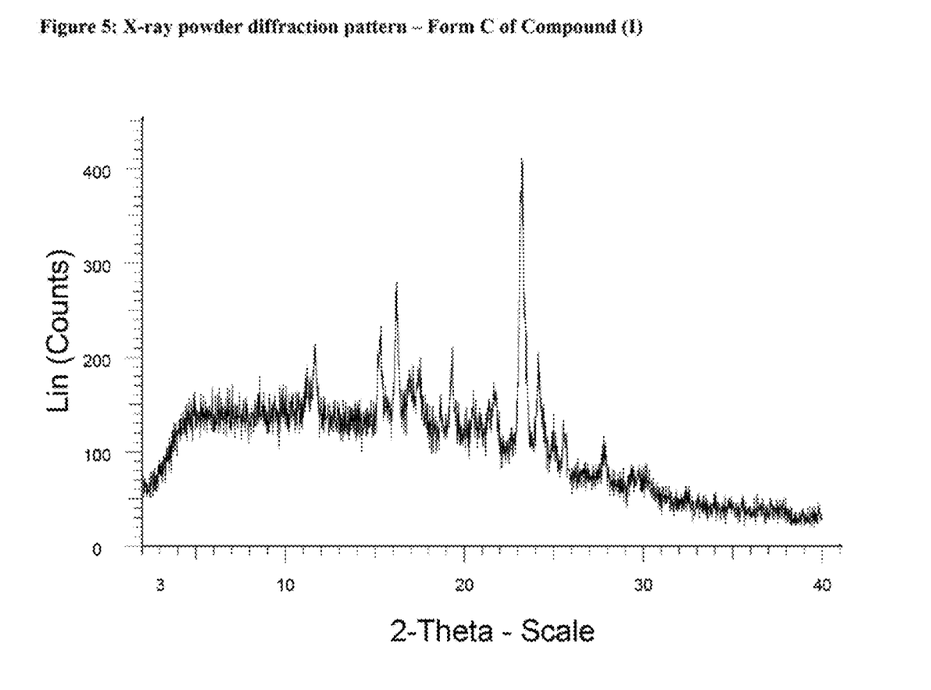
FIG. 5: X-ray powder diffraction pattern—Form C of Compound (I).

Form C of Compound (I) is characterised in providing at least one of the following 2θ values measured using CuKα radiation: 23.2 and 16.2. Compound (I) Form C is characterised in providing an X-ray powder diffraction pattern, substantially as shown in FIG. 5. Ten X-Ray powder diffraction peaks (using 1.54 Å X-rays, i.e. CuKα radiation) are shown in Table C:

TABLE C

| Ten X-Ray Powder Diffraction peaks for Form C of Compound (I) | | | | | | | | | |
|---|---|---|---|---|---|---|---|---|---|
| Angle (2θ): | 23.2 | 16.2 | 15.2 | 11.6 | 24.1 | 19.3 | 17.5 | 21.7 | 20.5 | 25.0 |
| Intensity (%): | 100 | 67.9 | 53.1 | 51.2 | 49.8 | 45.2 | 43.2 | 41.8 | 39.9 | 34.1 |

Accordingly there is provided Form C of Compound (I), which has an X-ray powder diffraction pattern with at least one specific peak at about 2-theta=23.2°.

Accordingly there is provided Form C of Compound (I), which has an X-ray powder diffraction pattern with at least one specific peak at about 2-theta=16.2°.

Accordingly there is provided Form C of Compound (I), which has an X-ray powder diffraction pattern with at least two specific peaks at about 2-theta=23.2° and 16.2°.

Accordingly there is provided Form C of Compound (I), which has an X-ray powder diffraction pattern with specific peaks at about 2-theta=23.2, 1.6.2, 15.2, 11.6, 24.1, 19.3, 17.5, 21.7, 20.5 and 25.0°.

Accordingly there is provided Form C of Compound (I) which has an X-ray powder diffraction pattern substantially the same as the X-ray powder diffraction pattern shown in FIG. 5.

Accordingly there is provided Form C of Compound (I), which has an X-ray powder diffraction pattern with at least one specific peak at 2-theta=23.2° plus or minus 0.2° 2-theta.

Accordingly there is provided Form C of Compound (I), which has an X-ray powder diffraction pattern with at least one specific peak at 2-theta=16.2° plus or minus 0.2° 2-theta.

Accordingly there is provided Form C of Compound (I), which has an X-ray powder diffraction pattern with at least two specific peaks at 2-theta=23.2° and 16.2° wherein said values may be plus or minus 0.2° 2-theta.

Accordingly there is provided Form C of Compound (I), which has an X-ray powder diffraction pattern with specific peaks at 2-theta=23.2, 16.2, 15.2, 11.6, 24.1, 19.3, 17.5, 21.7, 20.5 and 25.0° wherein said values may be plus or minus 0.2° 2-theta.

Accordingly there is provided Form C of Compound (I), which has an X-ray powder diffraction pattern with at least one specific peak at 2-theta=23.2°.

Accordingly there is provided Form C of Compound (I), which has an X-ray powder diffraction pattern with at least one specific peak at 2-theta=16.2°.

Accordingly there is provided Form C of Compound (I), which has an X-ray powder diffraction pattern with at least two specific peaks at 2-theta=15.0° and 19.2°.

Accordingly there is provided Form C of Compound (I), which has an X-ray powder diffraction pattern with specific peaks at 2-theta=23.2, 16.2, 15.2, 11.6, 24.1, 19.3, 17.5, 21.7, 20.5 and 25.0°.

Accordingly there is provided Form C of Compound (I), which has an X-ray powder diffraction pattern as shown in FIG. 5.

Figure 6:
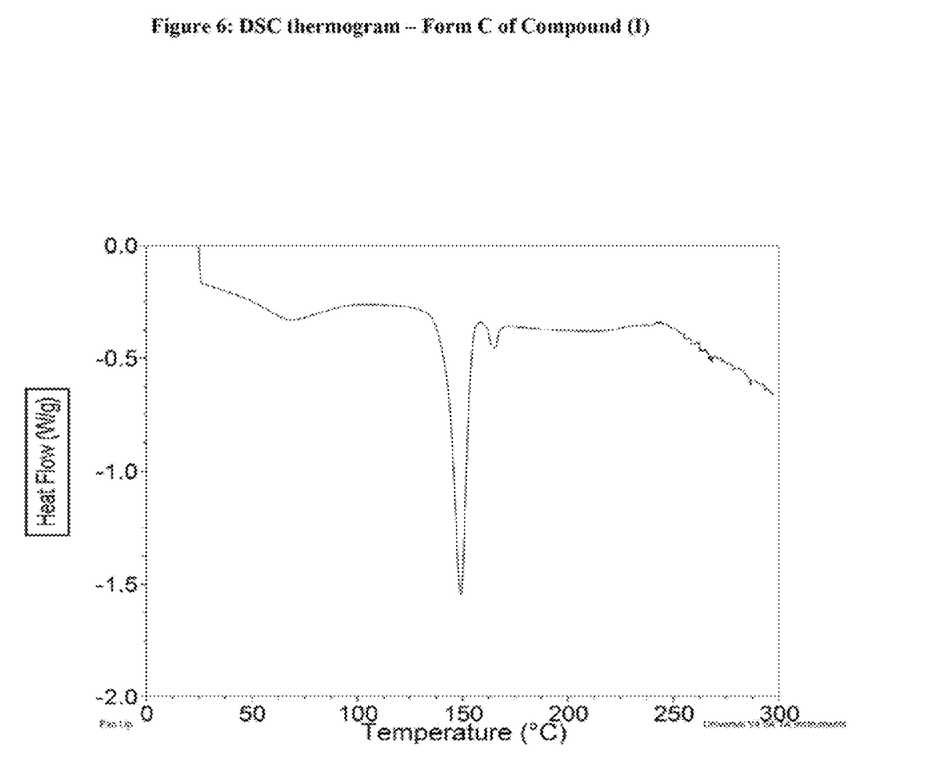
FIG. 6: DSC thermogram—Form C of Compound (I).

DSC analysis of Form C of Compound (I) shows a broad endotherm with an onset at 41.7° C. and a peak at 67.2° C. followed by a subsequent harp endotherm with an onset at 142.7° C. and a peak at 149.2° C. followed by a small endotherm with an onset of 161.6° C. and a peak at 164.5° C. (FIG. 6).

Form C of Compound (I) provides X-ray powder diffraction patterns substantially the same as the X-ray powder diffraction patterns shown in FIG. 5 and has the ten (angle 2-theta values) shown in Table C. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the Forms of the present invention are not limited to the crystals that provide X-ray powder diffraction patterns identical to the X-ray powder diffraction pattern shown in the Figures, and any crystals providing X-ray powder diffraction patterns substantially the same as those shown in the Figures fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 μm in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in the Figures and when reading the Tables. Furthermore, it should be understood that intensities might fluctuate depending on experimental conditions and sample preparation (preferred orientation).

According to a thither aspect of the invention there is provided a pharmaceutical composition, which comprises Compound (I) in crystalline form, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

A suitable formulation of Compound (I) in crystalline form is that where the compound is filled into a white hypromellose (HPMC) hard capsule with no other excipients. The strength of the drug product can range from 5 to 165 mg.

The composition of this capsule is as follows:

| Component | Quantity (per unit) | Function |
|---|---|---|
| Compound (I) | 5-165 mg (Note A) | Drug substance |
| White HPMC hard capsule (Note B) | 1 (size 0) | Capsule shell |

(Note A): The quantity of Compound (I) drug substance filled in the capsule is corrected for the potency of the batch being used.
(Note B): These HPMC-based capsule shells contain hypromellose, carrageenan, potassium chloride, titanium dioxide and carnauba wax. Each of these ingredients meet USP/NF, Ph Eur and JP or JPE standards.

An alternative suitable formulation of Compound (I) in crystalline form, (particularly Form B) is a tablet formulation, particularly a film-coated tablet formulation.

An example of a suitable film-coated tablet composition containing Compound (I) is described below:

| Substance (tablet core) | wt % within tablet core |
|---|---|
| Form B of Compound (I) | 60 |
| Microcrystalline cellulose | 25.88 |
| Mannitol | 8.63 |
| Croscarmellose sodium | 4 |
| Magnesium stearate | 1.5 (0.5 + 1.0)$^{Note\ C}$ |
| Substance (film coating) | wt % relative to tablet core |
| Opadry ™ II film coating | 3 |

$^{Note\ C}$As described in more detail below, the 0.5 wt % magnesium stearate is used in an intragranular context, while the remaining 1.0 wt % is used in an extragranular context Various sizes of tablets can be manufactured from a granule (described below) using conventional mixing, dry granulation, compression and film coating processes, according to Good Manufacturing Practice standards. For example, tablets containing from 50 mg to 500 mg of Compound (I) may be prepared using the above-mentioned composition using the methods described herein.

Granule preparation: Form B of Compound (I), microcrystalline cellulose, mannitol, croscarmellose sodium and intragranular magnesium stearate were mixed in a blender at 16 revolutions/minute for 5 minutes to achieve a uniform distribution of the Compound (I) within the mixture. This mixture was then fed through a roller compactor to produce a ribbon which was milled and passed through 1 mm screen to achieve uniform particle size of granule.

Tablet core preparation: The remaining extragranular magnesium stearate was added to the granules and the mixture was blended at 30 revolutions/minute for 1 minute. This mixture was then compressed into tablet cores using conventional tabletting equipment using standard concave punches to achieve the desired tablet sizes.

Film-coating of tablet cores: The compressed tablet cores were coated with an aqueous (purified water) suspension containing the Opadry™ II film coating components, using a perforated drum coater. The Opadry™ II film-coating material is available from Colorcon™ whose website is www.colorcon.com.

In one embodiment of the invention there is provided a pharmaceutical composition which comprises Compound (I) in crystalline form as described herein (particularly as Form B), in association with microcrystalline cellulose, mannitol, croscarmellose sodium and magnesium stearate.

In one embodiment there is provided a pharmaceutical tablet (i.e. suitable for oral administration to a human patient) which comprises from 50 to 500 mg of Compound (I) in crystalline form (particularly as Form B) as described herein, in association with one or more pharmaceutically acceptable excipients.

In one embodiment there is provided a pharmaceutical tablet (i.e. suitable for oral administration to a human patient) which comprises from 0.5 to 2% by weight of magnesium stearate, from 2 to 5% by weight of croscarmellose sodium, from 15 to 60% by weight of Compound (I) in crystalline form (particularly as Form B) as described herein, microcrystalline cellulose and mannitol, wherein the relative weights of microcrystalline cellulose and mannitol within the pharmaceutical tablet composition are in a ratio of between 3:1 and 1:1.

In one embodiment there is provided a pharmaceutical tablet (i.e. suitable for oral administration to a human patient) which comprises from 0.5 to 2% by weight of magnesium stearate, from 2 to 5% by weight of croscarmellose sodium, from 15 to 60% by weight of Compound (I) in crystalline form (particularly as Form B) as described herein, microcrystalline cellulose and mannitol, wherein the relative weights of microcrystalline cellulose and mannitol within the tablet are in a ratio of from 3:1 to 1:1 and wherein the amount of Compound (I) in crystalline form within the tablet is from 50 to 500 mg.

In any aspect, embodiment or claim referring to a tablet in this specification, the amount of Compound (I) in crystalline form within the tablet may be from 50 to 500 mg.

In one embodiment there is provided a pharmaceutical tablet (i.e. suitable for oral administration to a human patient) which comprises greater than 55% by weight of Compound (I) in crystalline form as described herein (particularly as Form B).

In one embodiment there is provided a pharmaceutical tablet (i.e. suitable for oral administration to a human patient) which comprises 50-70% by weight of Compound (I) in crystalline form as described herein (particularly as Form B).

Such tablet may comprise microcrystalline cellulose (particularly between 20 and 30% by weight of the total tablet).

Such tablet may comprise mannitol (particularly between 5 and 12% by weight of the total tablet).

Such tablet may comprise croscarmellose sodium (particularly between 2 and 5% by weight of the total tablet).

Such tablet may comprise magnesium stearate (particularly between 0.5 and 2% by weight of the total tablet).

Such tablet may include a film-coating around the core of the tablet (particularly where the film coating comprises 1 to 5% by weight of the total tablet).

Compound (I) in crystalline form will normally be administered to a warm-blooded animal at a unit dose within the range 5-5000 mg/m² body area of the animal, i.e. approximately 0.1-100 mg/kg, and this normally provides a therapeutically-effective dose. A unit dose thou such as a tablet or capsule will usually contain, for example 1-500 mg of active ingredient. Particular daily doses could be 400 mg b.i.d for monotherapy and 320 mg b.i.d (continuous) or 360 mg b.i.d (intermittent) for combination with another chemo-therapeutic. However the daily dose will necessarily be varied depending upon the host treated, the particular route of administration, and the severity of the illness being treated. Accordingly the practitioner who is treating any particular patient may determine the optimum dosage.

In the context of the present specification, the term "therapy" also includes "prophylaxis" unless there are specific indications to the contrary. The terms "therapeutic" and "therapeutically" should be construed accordingly.

As used herein, the term "treatment" is intended to have its normal everyday meaning of dealing with a disease in order to entirely or partially relieve one, some or all of its symptoms, or to correct or compensate for the underlying pathology.

As used herein, the term "prophylaxis" is intended to have its normal everyday meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

As a result of their PKB inhibitory activity, Compound (I) in crystalline form is expected to be useful in the treatment of diseases or medical conditions mediated alone or in part by PKB activity, for example cancer. The types of cancers which may be susceptible to treatment using Compound (I) in crystalline form of the present invention include, but are not limited to, ovarian cancer, cervical cancer, colorectal cancer, breast cancer, pancreatic cancer, glioma, glioblastoma, melanoma, prostate cancer, leukaemia, lymphoma, Non-Hodgkins lymphoma, gastric cancer, lung cancer, hepatocellular cancer, gastric cancer, gastrointestinal stromal tumour (GIST), glioma, thyroid cancer, bile duct cancer, endometrial cancer, renal cancer, anaplastic large cell lymphoma, acute myeloid leukaemia (AML), multiple myeloma, melanoma and mesothelioma. Breast cancer, and more specifically luminal breast cancer, may be particularly susceptible to treatment using compounds of the present invention. In particular Compound (I) in crystalline form may be useful in the treatment of breast cancer, including oestrogen receptor positive breast cancer, prostate cancer including castrate resistant prostate cancer and metastatic castrate resistant prostate cancer and gastric cancer. In one aspect of the invention Compound (I) in crystalline form may be useful in the treatment of breast cancer particularly oestrogen receptor positive breast cancer. In another aspect of the invention Compound (I) in crystalline form may be useful in the treatment of prostate cancer in particular castrate resistant prostate cancer. In a further aspect of the invention Compound (I) in crystalline form may be useful in the treatment of prostate cancer in particular metastatic castrate resistant prostate cancer. In another aspect of the invention Compound (I) in crystalline form may be useful in the treatment of gastric cancer.

It is envisaged that for the methods of treatment of cancer mentioned herein, Compound (I) in crystalline form will be administered to a mammal, more particularly a human being. Similarly, for the uses of Compound (I) in crystalline form for the treatment of cancer mentioned herein, it is envisaged that Compound (I) in crystalline form will be administered to a mammal, more particularly a human being.

According to a another aspect of the invention, there is therefore provided Compound (I) in crystalline form as defined hereinbefore, for use as a medicament.

According to a further aspect of the invention, there is provided Compound (I) in crystalline form as defined hereinbefore for use in the treatment of a disease mediated through PKB. According to a further aspect of the invention, there is provided Compound (I) in crystalline form as defined hereinbefore for use in the treatment of cancer. According to a further aspect of the invention, there is provided Compound (I) in crystalline form as defined hereinbefore for use in the treatment of breast cancer, including oestrogen receptor positive breast cancer, prostate cancer including castrate resistant prostate cancer and metastatic castrate resistant prostate cancer and gastric cancer.

According to a further aspect of the invention, there is provided the use of Compound (I) in crystalline form as defined hereinbefore for the preparation of a medicament for the treatment of a disease mediated through PKB. According to a further aspect of the invention, there is provided the use of Compound (I) in crystalline form as defined hereinbefore for the preparation of a medicament for the treatment of cancer. According to a further aspect of the invention, there is provided the use of Compound (I) in crystalline form as defined hereinbefore for the preparation of a medicament for the treatment of breast cancer, including oestrogen receptor positive breast cancer, prostate cancer including castrate resistant prostate cancer and metastatic castrate resistant prostate cancer and gastric cancer.

According to a further aspect of the invention, there is provided a method of treating a human suffering from a disease in which inhibition of PKB is beneficial, comprising the steps of administering to a person in need thereof of a therapeutically effective amount of Compound (I) in crystalline form as defined hereinbefore. In one embodiment of the invention there is provided a method of treating cancer which comprises the steps of administering to a person in need thereof of a therapeutically effective amount of Compound (I) in crystalline form as defined hereinbefore. In one embodiment of the invention there is provided a method of treating breast cancer, including oestrogen receptor positive breast cancer, prostate cancer including castrate resistant prostate cancer and metastatic castrate resistant prostate cancer and gastric cancer which comprises the steps of administering to a person in need thereof of a therapeutically effective amount of Compound (I) in crystalline form as defined hereinbefore.

In any embodiment, aspect or claim where "cancer" is mentioned, the cancer may be breast cancer.

In any embodiment, aspect or claim where "cancer" is mentioned, the cancer may be oestrogen receptor positive breast cancer.

In any embodiment, aspect or claim where "cancer" is mentioned, the cancer may be prostate cancer.

In any embodiment, aspect or claim where "cancer" is mentioned, the cancer may be castrate resistant prostate cancer.

In any embodiment, aspect or claim where "cancer" is mentioned, the cancer may be metastatic castrate resistant prostate cancer.

In any embodiment, aspect or claim where "cancer" is mentioned, the cancer may be gastric cancer.

The cancer treatment defined hereinbefore may be applied as a sole therapy or may involve, in addition to the compound of the invention, conventional surgery or radiotherapy or chemotherapy. Such chemotherapy may include a combination comprising Compound (I) in crystalline form with an androgen receptor signaling modulator selected from:

MDV-3100 (4-{3-[4-cyano-3-(trifluoromethyl)-phenyl]-5,5-dimethyl-4-oxo-2-thioxoimidazolidin-1-yl}-2-fluoro-N-methylbenzamide);

AZD3514 (1-{4-[2-(4-{1-[3-(trifluoromethyl)-7,8-dihydro[1,2,4]triazolo[4,3-b]pyrid-azin-6-yl]piperidin-4-yl}phenoxy)ethyl]piperazin-1-yl}ethanone);

abiraterone, or an ester prodrug thereof ((3β)-17-(pyridin-3-yl)androsta-5,16-dien-3-ol "abiraterone", or "abiraterone acetate"); and bicalutamide (N-[4-cyano-3-(trifluoromethyl)-phenyl]-3-[(4-fluorophenyl)-sulfonyl]-2-hydroxy-2-methylpropanamide);

or a pharmaceutically acceptable salt thereof.

MDV-3100 is alternatively known as "enzalutamide".

Such chemotherapy may also include a combination comprising Compound (I) in crystalline form and a taxane, particularly a taxane selected from docetaxel and paclitaxel.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial and/or synergistic effect of the combination.

In one embodiment of the invention there is provided a method of treating prostate cancer including castrate resistant prostate cancer and metastatic castrate resistant prostate cancer which comprises the steps of administering to a person in need thereof of a therapeutically effective amount of Compound (I) in crystalline form as defined hereinbefore in combination with an androgen receptor signaling modulator selected from:

MDV-3100 (4-{3-[4-cyano-3-(trifluoromethyl)-phenyl]-5,5-dimethyl-4-oxo-2-thioxoimidazolidin-1-yl}-2-fluoro-N-methylbenzamide);

AZD3514 (1-{4-[2-(4-{1-[3-(trifluoromethyl)-7,8-dihydro[1,2,4]triazolo[4,3-b]pyrid-azin-6-yl]piperidin-4-yl}phenoxy)ethyl]piperazin-1-yl}ethanone);

abiraterone, or an ester prodrug thereof ((3β)-17-(pyridin-3-yl)androsta-5,16-dien-3-ol "abiraterone", or "abiraterone acetate"); and bicalutamide (N-[4-cyano-3-(trifluoromethyl)-phenyl]-3-[(4-fluorophenyl)-sulfonyl]-2-hydroxy-2-methylpropanamide);

or a pharmaceutically acceptable salt thereof.

According to a further aspect of the invention, there is provided the use of Compound (I) in crystalline form as defined hereinbefore in combination with an androgen receptor signaling modulator selected from:

MDV-3100 (4-{3-[4-cyano-3-(trifluoromethyl)-phenyl]-5,5-dimethyl-4-oxo-2-thioxoimidazolidin-1-yl}-2-fluoro-N-methylbenzamide);

AZD3514 (1-{4-[2-(4-{1-[3-(trifluoromethyl)-7,8-dihydro[1,2,4]triazolo[4,3-b]pyrid-azin-6-yl]piperidin-4-yl}phenoxy)ethyl]piperazin-1-yl}ethanone);

abiraterone, or an ester prodrug thereof ((3β)-17-(pyridin-3-yl)androsta-5,16-dien-3-ol "abiraterone", or "abiraterone acetate"); and bicalutamide (N-[4-cyano-3-(trifluoromethyl)-phenyl]-3-[(4-fluorophenyl)-sulfonyl]-2-hydroxy-2-methylpropanamide);

or a pharmaceutically acceptable salt thereof; for the preparation of a medicament for the treatment of prostate cancer including castrate resistant prostate cancer and metastatic castrate resistant prostate cancer.

According to a further aspect of the invention, there is provided Compound (I) in crystalline form as defined hereinbefore in combination with an androgen receptor signaling modulator selected from:

MDV-3100 (4-{3-[4-cyano-3-(trifluoromethyl)-phenyl]-5,5-dimethyl-4-oxo-2-thioxoimidazolidin-1-yl}-2-fluoro-N-methylbenzamide);

AZD3514 (1-{4-[2-(4-{1-[3-(trifluoromethyl)-7,8-dihydro[1,2,4]triazolo[4,3-b]pyrid-azin-6-yl]piperidin-4-yl}phenoxy)ethyl]piperazin-1-yl}ethanone);

abiraterone, or an ester prodrug thereof ((3β)-17-(pyridin-3-yl)androsta-5,16-dien-3-ol "abiraterone", or "abiraterone acetate"); and bicalutamide (N-[4-cyano-3-(trifluoromethyl)-phenyl]-3-[(4-fluorophenyl)-sulfonyl]-2-hydroxy-2-methylpropanamide);

or a pharmaceutically acceptable salt thereof; for use in the treatment of prostate cancer including castrate resistant prostate cancer and metastatic castrate resistant prostate cancer.

In a further embodiment of the invention there is provided a method of treating breast cancer, including oestrogen receptor positive breast cancer, which comprises the steps of administering to a person in need thereof of a therapeutically effective amount of Compound (I) in crystalline form as defined hereinbefore in combination with a taxane, particularly a taxane selected from docetaxel and paclitaxel.

According to a further aspect of the invention, there is provided the use of Compound (I) in crystalline form as defined hereinbefore in combination with a taxane particularly a taxane selected from docetaxel and paclitaxel for the preparation of a medicament for the treatment of breast cancer, including oestrogen receptor positive breast cancer.

According to a further aspect of the invention, there is provided Compound (I) in crystalline form as defined hereinbefore in combination with a taxane, particularly a taxane selected from docetaxel and paclitaxel for use in the treatment of breast cancer, including oestrogen receptor positive breast cancer. In one embodiment the taxane is docetaxel. In another embodiment the taxane is paclitaxel.

17

LIST OF FIGURES

FIG. 3.1: X-ray powder diffraction pattern 1—Form B of Compound (I).
FIG. 3.2: X-ray powder diffraction pattern 2—Form B of Compound (I).

DETAILS OF TECHNIQUES USED

A Siemens D5000 X-Ray Powder Diffractometer was used to obtain X-ray diffraction data on Form A of Compound (I). The X-ray powder diffraction spectra were determined by mounting a sample of the crystalline material on a Siemens single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.54 Å (i.e. CuKα radiation). The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+ software.

A Bruker D8 X-ray powder diffractometer was used to obtain X-ray diffraction data on Forms B & C of Compound (I). The X-ray diffraction pattern of FIG. 3.1 (but not FIG. 3.2) for Form B was obtained using this diffractometer by mounting as sample of the crystalline material on as Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.54 Å (i.e. CuKα radiation). The collimated X-ray source was passed through a fixed divergence slit. The sample was exposed for 0.2 seconds per 0.014° 2-theta increment (continuous scan mode) over the range 2 degrees to 40 degrees 2-theta in theta-theta mode. The running time was approximately 9 minutes and 3 seconds. The instrument was equipped with a Position sensitive detector. Control and data capture was by means of a Dell Optiplex 686 NT 4.0 Workstation operating with Diffrac+ software.

A PANalytical CUBIX PRO X-ray powder diffractometer was used to analyse Form B of Compound (I). The X-ray diffraction pattern of FIG. 3.2 (but not FIG. 3.1) for Form B was obtained using this diffractometer by mounting a sample of the crystalline material on a single silicon crystal (SSC) wafer mount and spreading out the sample into a thin layer. The sample was spun at 30 revolutions per minute (to improve counting statistics) and irradiated with X-rays generated by a copper long-fine focus tube operated at 45 kV and 40 mA with a wavelength of 1.54 Å (i.e. CuKα radiation). The sample was exposed for 25 seconds per 0.025° 2-theta increment (continuous scan mode) over the range 2 degrees to 40 degrees 2-theta in theta-theta mode using an X'celerator detector (active length 2.55° 2θ).

A 'TA Instruments Q1000' Differential Scanning calorimeter was used to analyse Forms A, B and C of Compound (I). Typically less than 5 mg of material (contained in a standard aluminium pan fitted with a lid) was heated from 25-300° C. at a constant heating rate of 10° C./minute. A purge gas using nitrogen was used—flow rate 50 mL per minute.

Any crystal form that provides a XRPD diffractogram, Raman/IR spectrum, SSNMR spectrum or DSC thermogram substantially identical to those disclosed herein, fall within the scope of the present disclosures. One skilled in the art will have the ability to determine substantial identities of diffractograms, spectra and thermograms.

EXAMPLES

Reference Example 1

Preparation of Form A

WO 2009/047563 discloses three processes for the preparation of Compound (I)—Example 9 and alternative routes 1 and 2. "Example 9 alternative route 1" includes a slurry of Compound (I) in ethyl acetate, the other two processes isolate Compound (I) as a solid by evaporating fractions of a column. Three historical batches of Compound (I) from our compound collection synthesised using a procedure identical to, or substantially similar to, one of these three processes were analysed by XRD and all three identified as being a semi-crystalline form, designated as Form A, that bad a melting point of 155.2° C. (onset).

Example 1

Preparation of Form B

Approximately 20 mg of Compound (I) Form A was placed in a vial with as magnetic stirrer bar, and approximately 2 mL of acetonitrile added. The vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form B) was determined to be crystalline by XRPD. This material had a melting point of 162.3° C. (onset). An 1X-ray powder diffractogram of Form B prepared by this method is shown in FIG. 3.1.

Example 2

Preparation of Form C

Approximately 20 mg of Compound (I) Form A was placed in a vial with a magnetic flea, and approximately 2 mL of methanol added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form C) was determined to be semi-crystalline by XRPD. This material had a melting point of 1427° C. (onset) and a peak at about 149.2° C., followed by a further melting endotherm with an onset of 161.6° C. and a peak at 164.5° C.

Example 3

Alternative Preparation of Form B

The initially produced Form A of Compound (I) may be converted to Form B using the following process: Compound (I) is mixed with 7-8 relative volumes of absolute ethanol and the mixture is then heated to 70-75° C. under reflux. The mixture is then filtered to remove undissolved particulate matter and the filtrate is cooled to 60-65° C. A small amount of previously prepared seed (e.g. 0.5 wt % of Form B of Compound (I)) is then added to the mixture. The fluid surrounding the reaction vessel is then cooled to −10° C. at a cooling rate of 0.3° C./minute and then the mixture is stirred for a further 8-12 hours before the resulting solid is isolated by filtration. This wet solid is then dried under vacuum at a temperature of 60-65° C. to provide Form B of Compound (I). An X-ray powder diffractogram of Form B prepared by this method is shown in FIG. 3.2. DSC analysis of Form B of Compound (I) as prepared by this method, shows a melting endotherm with an onset of 168.5° C. and a peak at 171.0° C. (FIG. 7). For the avoidance of doubt, one "relative volume" means that mL of a liquid is used be used per 1 g of compound.

I claim:

1. (S)-4-Amino-N-(1-(4-chlorophenyl)-3-hydroxypropyl)-1-(7H-pyrrolo[2,3-d]-pyrimidin-4-yl)piperidine-4-carboxamide crystalline Form B which is characterized by an X-ray powder diffraction pattern with peaks at about 2-theta=10.0, 12.3, 15.0, 17.1, 19.2 and 24.4°.

2. (S)-4-Amino-N-(1-(4-chlorophenyl)-3-hydroxypropyl)-1-(7H-pyrrolo[2,3-d]-pyrimidin-4-yl)piperidine-4-carboxamide crystalline Form B which is characterized by an X-ray powder diffraction pattern with at least ten peaks at about 2-theta=15.0, 19.2, 12.3, 10.0, 17.1, 24.4, 16.4, 26.0, 15.5, and 23.9°.

3. (S)-4-Amino-N-(1-(4-chlorophenyl)-3-hydroxypropyl)-1-(7H-pyrrolo[2,3-d]-pyrimidin-4-yl)piperidine-4-carboxamide crystalline Form B which is characterized by an X-ray powder diffraction pattern with at least ten peaks at about 2-theta=10.0, 5.0, 15.0, 19.2, 17.1, 12.3, 24.4, 30.2, 32.3, and 23.3°.

4. A pharmaceutical composition comprising (S)-4-Amino-N-(1-(4-chlorophenyl)-3-hydroxypropyl)-1-(7H-pyrrolo[2,3-d]-pyrimidin-4-yl)piperidine-4-carboxamide crystalline Form B, according to claim 1, in association with and a pharmaceutically-acceptable diluent or carrier.

5. A pharmaceutical composition comprising (S)-4-Amino-N-(1-(4-chlorophenyl)-3-hydroxypropyl)-1-(7H-pyrrolo[2,3-d]-pyrimidin-4-yl)piperidine-4-carboxamide crystalline Form B, according to claim 2, in association with and a pharmaceutically-acceptable diluent or carrier.

6. A pharmaceutical composition comprising (S)-4-Amino-N-(1-(4-chlorophenyl)-3-hydroxypropyl)-1-(7H-pyrrolo[2,3-d]-pyrimidin-4-yl)piperidine-4-carboxamide crystalline Form B, according to claim 3, in association with and a pharmaceutically-acceptable diluent or carrier.

7. The pharmaceutical composition according to claim 4, further comprising microcrystalline cellulose, mannitol, croscarmellose sodium and magnesium stearate.

8. The pharmaceutical composition according to claim 5, further comprising microcrystalline cellulose, mannitol, croscarmellose sodium and magnesium stearate.

9. The pharmaceutical composition according to claim 6, further comprising microcrystalline cellulose, mannitol, croscarmellose sodium and magnesium stearate.

10. A pharmaceutical tablet comprising from 0.5 to 2% by weight of magnesium stearate, from 2 to 5% by weight of croscarmellose sodium, from 15 to 60% by weight of crystalline Form B according to claim 1, microcrystalline cellulose and mannitol, wherein the relative weights of microcrystalline cellulose and mannitol within the tablet are in a ratio of from 3:1 to 1:1, and wherein the amount of crystalline Form B within the tablet is from 50 to 500 mg.

11. A pharmaceutical tablet comprising from 0.5 to 2% by weight of magnesium stearate, from 2 to 5% by weight of croscarmellose sodium, from 15 to 60% by weight of crystalline Form B according to claim 2, microcrystalline cellulose and mannitol, wherein the relative weights of microcrystalline cellulose and mannitol within the tablet are in a ratio of from 3:1 to 1:1, and wherein the amount of crystalline Form B within the tablet is from 50 to 500 mg.

12. A pharmaceutical tablet comprising from 0.5 to 2% by weight of magnesium stearate, from 2 to 5% by weight of croscarmellose sodium, from 15 to 60% by weight of crystalline Form B according to claim 3, microcrystalline cellulose and mannitol, wherein the relative weights of microcrystalline cellulose and mannitol within the tablet are in a ratio of from 3:1 to 1:1, and wherein the amount of crystalline Form B within the tablet is from 50 to 500 mg.

* * * * *